(12) United States Patent
Rabe et al.

(10) Patent No.: US 9,216,145 B2
(45) Date of Patent: Dec. 22, 2015

(54) SEMI-PERMANENT COSMETIC CONCEALER

(75) Inventors: Thomas Elliott Rabe, Baltimore, MD (US); James Herman Dempsey, Danbury, CT (US)

(73) Assignee: The Procter & Gamble Company, Cincinnati, OH (US)

( * ) Notice: Subject to any disclaimer, the term of this patent is extended or adjusted under 35 U.S.C. 154(b) by 101 days.

(21) Appl. No.: 13/457,173

(22) Filed: Apr. 26, 2012

(65) Prior Publication Data

US 2012/0269753 A1 Oct. 25, 2012

Related U.S. Application Data (63) Continuation-in-part of application No. 13/274,852, filed on Oct. 17, 2011, and a continuation-in-part of application No. 12/912,478, filed on Oct. 26, 2010.

(60) Provisional application No. 61/455,843, filed on Oct. 27, 2010, provisional application No. 61/255,457, filed on Oct. 27, 2009.

(51) Int. Cl.

| | |
|---|---|
| *A61K 8/02* | (2006.01) |
| *A61K 8/31* | (2006.01) |
| *A61K 8/19* | (2006.01) |
| *A61K 8/92* | (2006.01) |
| *A61Q 1/10* | (2006.01) |
| *A61K 8/37* | (2006.01) |
| *A61K 8/58* | (2006.01) |

(52) U.S. Cl.
CPC ............... *A61K 8/31* (2013.01); *A61K 8/0241* (2013.01); *A61K 8/19* (2013.01); *A61K 8/375* (2013.01); *A61K 8/585* (2013.01); *A61K 8/922* (2013.01); *A61Q 1/10* (2013.01)

(58) Field of Classification Search
CPC ........................................................ A61Q 1/10
See application file for complete search history.

(56) References Cited

U.S. PATENT DOCUMENTS

| | | | |
|---|---|---|---|
| 2,458,063 | A | 1/1949 | Duhlberg |
| 2,831,854 | A | 4/1958 | Tucker |
| 2,900,306 | A | 8/1959 | Slater |
| 3,255,082 | A | 6/1966 | Barton |
| 3,677,271 | A | 7/1972 | Luciano |
| 3,690,777 | A | 9/1972 | Costa |
| 3,739,789 | A | 6/1973 | Cataneo |
| 3,802,841 | A | 4/1974 | Robin |
| 3,963,699 | A | 6/1976 | Rizzi et al. |
| 4,005,195 | A | 1/1977 | Jandacek |
| 4,005,196 | A | 1/1977 | Jandacek et al. |
| 4,126,679 | A | 11/1978 | Davy et al. |
| 4,137,306 | A | 1/1979 | Rubino et al. |
| 4,151,272 | A | 4/1979 | Geary et al. |
| 4,154,816 | A | 5/1979 | Roehl et al. |
| D252,911 | S | 9/1979 | Levy |
| 4,202,879 | A | 5/1980 | Shelton |
| 4,226,889 | A | 10/1980 | Yuhas |
| 4,228,277 | A | 10/1980 | Landoll |
| 4,229,432 | A | 10/1980 | Geria |
| 4,280,994 | A | 7/1981 | Turney |
| 4,322,400 | A | 3/1982 | Yuhas |
| 4,336,246 | A | 6/1982 | Leon-Pekarek |
| 4,346,079 | A | 8/1982 | Roehl |
| 4,383,988 | A | 5/1983 | Teng et al. |
| D277,324 | S | 1/1985 | Davey |
| 4,517,360 | A | 5/1985 | Volpenhein |
| 4,518,772 | A | 5/1985 | Volpenhein |
| 4,725,432 | A | 2/1988 | May |
| 4,759,924 | A | 7/1988 | Luebbe et al. |
| 4,797,300 | A | 1/1989 | Jandacek et al. |
| 4,816,261 | A | 3/1989 | Luebbe et al. |
| 4,886,080 | A | 12/1989 | Cole |
| 4,932,802 | A | 6/1990 | Cantone |
| 4,980,155 | A | 12/1990 | Shah et al. |
| 5,017,398 | A | 5/1991 | Jandacek et al. |
| 5,019,375 | A | 5/1991 | Tanner et al. |
| 5,040,914 | A | 8/1991 | Fitjer |
| 5,097,853 | A | 3/1992 | Nehashi |
| 5,104,646 | A | 4/1992 | Bolich, Jr. et al. |
| RE33,996 | E | 7/1992 | Jandacek |
| 5,165,917 | A | 11/1992 | Zabotto |
| 5,193,918 | A | 3/1993 | Lohrmann et al. |
| 5,306,514 | A | 4/1994 | Letton et al. |
| 5,306,515 | A | 4/1994 | Letton et al. |

(Continued)

FOREIGN PATENT DOCUMENTS

| | | |
|---|---|---|
| CN | 300856708 | 12/2008 |
| CN | 300856709 | 12/2008 |

(Continued)

OTHER PUBLICATIONS

PCT International Search Report and Written Opinion for PCT/US2013/038339 dated Sep. 12, 2013.
R. Pigeon and P. Allard, Chimie Macromo-culaire Applique, 40141 (1974), pp. 139-158 (No. 600).
PCT International Search Report and Written Opinion for PCT/US2012/038231 dated Aug. 21, 2012.
Avon, Avon Colour, In a Blink Eye Shadow and Liner, date published Mar. 2007; www.gnpd.com, 2 pages.
Avon, Avon, Blueberry Cool/Black Lush Lips and Long Lashes, date published Mar. 2006; www.gnpd.com, 2 pages.
Avon, Avon, Dual Ended Eye-Liner, date published Oct. 2007; www.gnpd.com, 2 pages.
Avon, Avon, Shimmer Shadow and Liner, date published Jun. 2007; www.gnpd.com, 2 pages.

(Continued)

*Primary Examiner* — Hasan Ahmed
(74) *Attorney, Agent, or Firm* — Betty J. Zea (57) ABSTRACT

A semi-permanent concealer composition for use on a target skin area that includes from about 10% to about 80% of a non-aqueous carrier from about 15% to about 35% of a tackifier comprising a tall oil glyceride, and from about 0.1% to about 20%, by weight, of colorant particles. The semi-permanent concealer composition is long lasting and has excellent wear characteristics.

4 Claims, 3 Drawing Sheets
(2 of 3 Drawing Sheet(s) Filed in Color)

(56) References Cited

U.S. PATENT DOCUMENTS

| | | |
|---|---|---|
| 5,306,516 A | 4/1994 | Letton et al. |
| RE34,617 E | 5/1994 | Jandacek et al. |
| 5,376,231 A | 12/1994 | Matsumoto et al. |
| 5,389,363 A | 2/1995 | Snyder |
| D360,486 S | 7/1995 | Schultz |
| 5,490,529 A | 2/1996 | Fitjer |
| 5,794,632 A | 8/1998 | Gueret |
| 5,832,942 A | 11/1998 | Gutberlet |
| 5,866,434 A | 2/1999 | Massey et al. |
| 5,996,780 A * | 12/1999 | Gurrera .................. 206/209 |
| D422,748 S | 4/2000 | Lang |
| 6,071,503 A | 6/2000 | Drechsler et al. |
| 6,074,654 A | 6/2000 | Drechsler et al. |
| 6,080,687 A | 6/2000 | Ishwarlal |
| 6,139,823 A | 10/2000 | Drechsler et al. |
| 6,200,045 B1 | 3/2001 | Hahn et al. |
| 6,203,814 B1 | 3/2001 | Fisher et al. |
| 6,241,408 B1 | 6/2001 | Lang |
| 6,267,951 B1 | 7/2001 | Shah et al. |
| 6,303,105 B1 | 10/2001 | Shah et al. |
| D450,888 S | 11/2001 | Breidenbach et al. |
| 6,340,466 B1 | 1/2002 | Drechsler et al. |
| D453,588 S | 2/2002 | Breidenbach et al. |
| D453,589 S | 2/2002 | Breidenbach et al. |
| 6,450,179 B2 | 9/2002 | Bengis |
| 6,464,418 B1 | 10/2002 | Visser et al. |
| 6,488,427 B1 | 12/2002 | Breidenbach et al. |
| 6,491,902 B2 | 12/2002 | Shefer et al. |
| 6,500,446 B1 | 12/2002 | Derrieu et al. |
| D474,341 S | 5/2003 | Cantone et al. |
| 6,612,764 B2 | 9/2003 | Dumler et al. |
| 6,637,963 B2 | 10/2003 | Huang |
| D482,284 S | 11/2003 | Cantone et al. |
| 6,682,242 B1 | 1/2004 | Montoli |
| D497,455 S | 10/2004 | Lee |
| 6,811,770 B2 | 11/2004 | Ferrari et al. |
| 6,979,440 B2 | 12/2005 | Shefer et al. |
| 6,985,879 B2 | 1/2006 | Walker et al. |
| 7,077,591 B2 | 7/2006 | Gueret |
| D530,857 S | 10/2006 | Black |
| 7,168,875 B1 | 1/2007 | Zhang et al. |
| 7,175,359 B2 | 2/2007 | Zhang et al. |
| 7,186,274 B2 | 3/2007 | Vic Gabin et al. |
| D542,978 S | 5/2007 | Bortolotti |
| 7,210,870 B2 | 5/2007 | Breidenbach et al. |
| 7,226,227 B2 | 6/2007 | Gueret |
| 7,241,835 B2 | 7/2007 | O'Brien et al. |
| 7,276,088 B2 | 10/2007 | Huang et al. |
| D561,390 S | 2/2008 | Sugawara |
| D566,335 S | 4/2008 | Althoff et al. |
| D566,337 S | 4/2008 | Althoff et al. |
| D574,154 S | 8/2008 | Dumler et al. |
| D574,155 S | 8/2008 | Dumler et al. |
| D578,770 S | 10/2008 | Berhault |
| D579,208 S | 10/2008 | Berhault |
| 7,438,953 B2 | 10/2008 | Kotov et al. |
| D581,169 S | 11/2008 | Berhault |
| D583,506 S | 12/2008 | Justice |
| D585,600 S | 1/2009 | Althoff et al. |
| 7,473,045 B2 | 1/2009 | Dumler |
| D592,858 S | 5/2009 | Berhault |
| D593,330 S | 6/2009 | Berhault |
| D593,331 S | 6/2009 | Berhault |
| D598,657 S | 8/2009 | Berhault |
| D600,921 S | 9/2009 | Berhault |
| D600,922 S | 9/2009 | Berhault |
| D600,923 S | 9/2009 | Berhault |
| 7,632,489 B2 | 12/2009 | Wyatt et al. |
| D615,419 S | 5/2010 | Owen |
| 7,780,875 B2 | 8/2010 | Asgari |
| 7,842,285 B2 | 11/2010 | Lu et al. |
| 7,856,806 B1 | 12/2010 | Chasman et al. |
| D634,127 S | 3/2011 | Burgess et al. |
| D634,478 S | 3/2011 | Kolas et al. |
| D636,940 S | 4/2011 | Acierto et al. |
| D642,805 S | 8/2011 | Burgess et al. |
| 7,993,661 B2 | 8/2011 | Arnaud et al. |
| D653,398 S | 1/2012 | Acierto et al. |
| 8,096,306 B2 | 1/2012 | Malvar et al. |
| D654,626 S | 2/2012 | Kolas et al. |
| 8,168,095 B2 | 5/2012 | Alberius et al. |
| 8,298,494 B2 | 10/2012 | Komiya et al. |
| 8,323,628 B2 | 12/2012 | Atis |
| 8,329,147 B2 | 12/2012 | Ansmann et al. |
| 8,336,560 B2 | 12/2012 | Dumler et al. |
| 8,444,930 B2 | 5/2013 | Komiya et al. |
| 2001/0051168 A1 | 12/2001 | Ramin et al. |
| 2002/0071707 A1 | 6/2002 | Breidenbach |
| 2002/0076390 A1 | 6/2002 | Kantner et al. |
| 2002/0083954 A1 | 7/2002 | Gavney |
| 2002/0185148 A1 | 12/2002 | Bengis |
| 2002/0190336 A1 | 12/2002 | Shimizu et al. |
| 2003/0041870 A1 | 3/2003 | Su |
| 2003/0086741 A1 | 5/2003 | Kim |
| 2003/0095935 A1 | 5/2003 | Chaiyawat et al. |
| 2003/0143181 A1 | 7/2003 | Hensen et al. |
| 2004/0105828 A1 | 6/2004 | Chaiyawat et al. |
| 2004/0115232 A1 | 6/2004 | Giroud et al. |
| 2004/0126303 A1 | 7/2004 | Hwang |
| 2004/0190974 A1 | 9/2004 | Cantone et al. |
| 2004/0228890 A1 | 11/2004 | Blin et al. |
| 2004/0234564 A1 | 11/2004 | Blin et al. |
| 2005/0095213 A1 | 5/2005 | Blin et al. |
| 2005/0176598 A1 | 8/2005 | Bergquist et al. |
| 2005/0186167 A1 | 8/2005 | Ueda et al. |
| 2005/0276779 A1 | 12/2005 | Blin |
| 2006/0029560 A1 | 2/2006 | Blin |
| 2006/0067783 A1 | 3/2006 | Tsaur |
| 2006/0127339 A1 | 6/2006 | Bavouzet et al. |
| 2006/0134035 A1 | 6/2006 | Zheng et al. |
| 2006/0189554 A1 | 8/2006 | Mumper et al. |
| 2006/0260633 A1 | 11/2006 | Wyatt et al. |
| 2006/0275232 A1 | 12/2006 | Chevalier |
| 2006/0275235 A1 * | 12/2006 | Takeda et al. .............. 424/70.13 |
| 2007/0020205 A1 * | 1/2007 | Blin et al. .................. 424/61 |
| 2007/0041920 A1 | 2/2007 | Blin et al. |
| 2007/0048238 A1 | 3/2007 | Sandewicz et al. |
| 2007/0140991 A1 | 6/2007 | Maitra et al. |
| 2007/0274941 A9 | 11/2007 | Blin |
| 2007/0286824 A1 | 12/2007 | Rabe et al. |
| 2008/0000491 A1 | 1/2008 | Bodelin |
| 2008/0014232 A1 | 1/2008 | Arnaud et al. |
| 2008/0031834 A1 * | 2/2008 | Manelski et al. .............. 424/59 |
| 2008/0056807 A1 | 3/2008 | Vintimiglia |
| 2008/0107615 A1 | 5/2008 | Keene et al. |
| 2008/0115798 A1 | 5/2008 | Rainey et al. |
| 2008/0124350 A1 | 5/2008 | Mumper et al. |
| 2008/0171009 A1 | 7/2008 | Auguste et al. |
| 2008/0226575 A1 | 9/2008 | Hanna |
| 2008/0311063 A1 | 12/2008 | Shah et al. |
| 2009/0010868 A1 | 1/2009 | Ilekti et al. |
| 2009/0098170 A1 | 4/2009 | D'Acchioli et al. |
| 2009/0142282 A1 | 6/2009 | Kendall et al. |
| 2009/0193692 A1 | 8/2009 | Lipczynski |
| 2009/0263658 A1 | 10/2009 | Alberius et al. |
| 2009/0317350 A1 | 12/2009 | Lu et al. |
| 2010/0003205 A1 | 1/2010 | Elliott et al. |
| 2010/0003293 A1 | 1/2010 | Elliott et al. |
| 2010/0028612 A1 | 2/2010 | Gruber et al. |
| 2010/0068163 A1 | 3/2010 | Lu |
| 2010/0074928 A1 | 3/2010 | Elliott et al. |
| 2010/0152135 A1 | 6/2010 | Blin |
| 2010/0179105 A1 | 7/2010 | Blin et al. |
| 2011/0094533 A1 | 4/2011 | Dempsey et al. |
| 2011/0094914 A1 | 4/2011 | Dempsey et al. |
| 2011/0117040 A1 | 5/2011 | Dempsey et al. |
| 2011/0117043 A1 | 5/2011 | Dempsey et al. |
| 2011/0268490 A1 | 11/2011 | Acierto et al. |
| 2012/0114585 A1 | 5/2012 | Dempsey et al. |
| 2012/0269753 A1 | 10/2012 | Rabe et al. |
| 2012/0298128 A1 | 11/2012 | Hodgetts et al. |
| 2012/0315076 A1 | 12/2012 | Bekele et al. |
| 2013/0012594 A1 | 1/2013 | Hirasawa et al. |

(56) References Cited

U.S. PATENT DOCUMENTS

| | | |
|---|---|---|
| 2013/0056016 A1 | 3/2013 | Guay et al. |
| 2013/0056019 A1 | 3/2013 | Wilson et al. |
| 2013/0056020 A1 | 3/2013 | Wilson et al. |

FOREIGN PATENT DOCUMENTS

| | | |
|---|---|---|
| CN | 300856710 | 12/2008 |
| CN | 102360418 A | 2/2012 |
| DE | 3923731 A1 | 1/1991 |
| EM | 000345483.003 | 7/2005 |
| EM | 000386388.0001 | 11/2005 |
| EM | 000386388.0002 | 11/2005 |
| EM | 000386388.0020 | 11/2005 |
| EM | 000386388.0028 | 11/2005 |
| EM | 000386388.0030 | 11/2005 |
| EM | 000386388.0031 | 11/2005 |
| EM | 000386388.0034 | 11/2005 |
| EM | 000500418.001 | 5/2006 |
| EM | 000540869.0021 | 7/2006 |
| EM | 000540869.0024 | 7/2006 |
| EM | 000603808.002 | 11/2006 |
| EM | 000623202.0002 | 12/2006 |
| EM | 000623202.0004 | 12/2006 |
| EM | 000623202.0009 | 12/2006 |
| EM | 000623202.0010 | 12/2006 |
| EM | 000623202.0011 | 12/2006 |
| EM | 000623202.0012 | 12/2006 |
| EM | 000623202.0013 | 12/2006 |
| EM | 000614706.001 | 1/2007 |
| EM | 000654272.0003 | 4/2007 |
| EM | 000654272.0004 | 4/2007 |
| EM | 000654272.0005 | 4/2007 |
| EM | 000688007.0002 | 4/2007 |
| EM | 000688007.0003 | 4/2007 |
| EM | 000871017.0001 | 2/2008 |
| EM | 000871017.0007 | 2/2008 |
| EM | 000871017.0008 | 2/2008 |
| EM | 000871017.0009 | 2/2008 |
| EM | 000871017.0010 | 2/2008 |
| EM | 000871017.0014 | 2/2008 |
| EM | 000871017.0015 | 2/2008 |
| EM | 000871017.0016 | 2/2008 |
| EM | 000871017.0024 | 2/2008 |
| EM | 000871017.0025 | 2/2008 |
| EM | 000871017.0026 | 2/2008 |
| EM | 000871017.0027 | 2/2008 |
| EM | 000871017.0028 | 2/2008 |
| EM | 000871017.0029 | 2/2008 |
| EM | 000871017.0030 | 2/2008 |
| EM | 000871017.0031 | 2/2008 |
| EM | 000871017.0032 | 2/2008 |
| EM | 000871017.0033 | 2/2008 |
| EM | 000871017.0037 | 2/2008 |
| EM | 000871017.0038 | 2/2008 |
| EM | 000871017.0039 | 2/2008 |
| EM | 000871017.0040 | 2/2008 |
| EM | 000871017.0043 | 2/2008 |
| EM | 000871017.0044 | 2/2008 |
| EM | 000871017.0054 | 2/2008 |
| EM | 000871017.0055 | 2/2008 |
| EM | 000871017.0056 | 2/2008 |
| EM | 000871017.0057 | 2/2008 |
| EM | 000871017.0058 | 2/2008 |
| EM | 000871017.0059 | 2/2008 |
| EM | 000871017.0060 | 2/2008 |
| EM | 000871017.0061 | 2/2008 |
| EP | 0024365 B1 | 3/1981 |
| EP | 549494 | 6/1993 |
| EP | 1238603 A3 | 9/2003 |
| FR | 2079785 | 10/1971 |
| FR | 000975286.0001 | 12/1997 |
| FR | 2898469 A1 | 9/2007 |
| FR | 2919477 A1 | 2/2009 |
| GB | 2124081 A | 2/1984 |
| GB | 2293545 A | 4/1996 |
| JP | 03173811 | 7/1991 |
| JP | 2004188189 A | 7/2004 |
| JP | 2004238363 | 8/2004 |
| JP | 2004339212 A | 12/2004 |
| JP | 2006174936 A | 7/2006 |
| JP | 2006282585 | 10/2006 |
| JP | 0D1207926 | 5/2007 |
| JP | 2009114099 | 5/2009 |
| JP | 2009137841 | 6/2009 |
| KR | 300402225 | 12/2005 |
| KR | 300424071.0001 | 2/2006 |
| KR | 300465977 | 10/2007 |
| KR | 300488446 | 4/2008 |
| KR | 300507379 | 9/2008 |
| WO | 000011033.003 | 7/1988 |
| WO | 000014434.0010 | 10/1989 |
| WO | 000014434.0011 | 10/1989 |
| WO | 000014434.0025 | 10/1989 |
| WO | 96/20698 | 7/1996 |
| WO | 000042185.0001 | 2/1998 |
| WO | 000042185.0002 | 2/1998 |
| WO | 000042185.0003 | 2/1998 |
| WO | 00042185.0004 | 2/1998 |
| WO | 00/47177 | 8/2000 |
| WO | 000054973.0006 | 3/2001 |
| WO | 01/45652 | 6/2001 |
| WO | 2004073662 A1 | 9/2004 |
| WO | 2006/058795 | 6/2006 |
| WO | 2006/078541 | 7/2006 |
| WO | WO 2007040517 * 4/2007 ............... A61Q 1/10 |
| WO | 2008/074870 A2 | 6/2008 |
| WO | 2008089926 A | 7/2008 |
| WO | 2012/011043 A1 | 1/2012 |

OTHER PUBLICATIONS

Avon, MistakeProof Mascara, date published Oct. 2008; www.gnpd.com , 4pages.
Bare Escentuals, bareMinerals Tutorials, Lesson 1: Get Cheeky, date published Feb. 2008; www.gnpd.com, 1 page.
Bare Escentuals, bareMinerals, Get Started: Eyes, Cheeks, Lips Set, date published Mar. 2008; www.gnpd.com, 1 page.
Bobbi Brown Copper Diamond, Everything/Lash Glamour Mascara Duo, date published Nov. 2008; www.gnpd.com, 3 pages.
Bobbi Brown, Bobbi Brown Christmas 2008, Night Sky Long-Wear Eye Palette, date published Dec. 2008; www.gnpd.com, 3 pages.
Bobbi Brown, Honey Glaze Long-Wear Eye Palette, date published Apr. 2009; www.gnpd.com, 3 pages.
Bobbi Brown, Lip and Eye Basics Palette, date published Sep. 2006; www.gnpd.com, 2 pages.
Bobbi Brown, Shimmering Nudes Collection, Shimmering Nudes Palette, date published Oct. 2008; www.gnpd.com, 3 pages.
Caboodles Color Tips, Mascara Extension, date published Dec. 2005; www.gnpd.com, 2 pages.
Cosmetobelleza Natural IM , Double Effect Mascara, date published: Jul. 2009; www.gnpd.com, 2 pages.
Creative Brands, Australis, Eyeshadow, date published Aug. 2007; www.gnpd.com, 2 pages.
Del Laboratories, Sally Hansen Healing Beauty, Thicken-Up Plumper+Mascara, date published Oct. 2003; www.gnpd.com, 2 pages.
Gurwitch Products, Laura Mercier, Limited-Edition Eye Book, date published Dec. 2008; www.gnpd.com, 2 pages.
Gurwitch Products, Laura Mercier, Beauty Library Set, date published Dec. 2006; www.gnpd.com, 3 pages.
Helena Rubinstein, Surrealist Mascara & Liner, date published Nov. 2006; www.gnpd.com, 2 pages.
Invima, Isadora Wonder Full Mascara, date published Sep. 2006; www.gnpd.com, 2 pages.
Kao, Aube Couture, Designing Double Mascara, date published Dec. 2008; www.gnpd.com, 3 pages.
Isehan, Kiss Me Mascara Remover, date published Sep. 2008; www-w.gnpd.com, 2 pages.
Kose, Fasio Easy Mascara Remover, date published Jun. 2009; www-w.gnpd.com, 3 pages.

(56) References Cited

OTHER PUBLICATIONS

Kose, Fasio Mascara Easy Remover, date published Jan. 2009; wwww.gnpd.com, 2 pages.
Lorac Cosmetics, Lorac, Fairytale Life Makeup Collection, date published Dec. 2007; www.gnpd.com; 4 pages.
L'Oreal Double Mascara, Date published May 2006; www.gnpd.com, 2 pages.
MAQuillAGE Shisiedo, Mascara Remover, date published Jun. 2008; wwww.gnpd.com, 2 pages.
Napoleon Perdis Cosmetics, NP Set Eyeliner, date published Mar. 2009; www.gnpd.com, 4 pages.
Napoleon Perdis Cosmetics, NP Set, Eye Palette, date published Feb. 2009 www.gnpd.com, 3 pages.
Prestige Cosmetics, Glitter Lash Mascara, date published Dec. 2008, www.gnpd.com, 2 pages.
Revlon, Limited Edition Dual Lash Mystique Mascara, date published Jun. 2003; www.gnpd.com, 1 page.
Rimmel, Coty, Volume Extend Waterproof Mascara, date published Sep. 2006; www.gnpd.com, 2 pages.
Rimmel, Double Play Multi Look Mascara, date published Apr. 2007; Mar. 2007; www.gnpd.com, 2 pages.
Rossman, Rival de Loop Young, Double Brush Mascara, date published: Oct. 2009; www.gnpd.com, 2 pages.
Shiseido, The Makeup Eraser Pencil, date published Jun. 2001; wwww.gnpd.com, 2 pages.
Sleek Makeup, Duo Dip it Mascara+Eyeliner, date published Mar. 27, 2009; www.gnpd.com, 3 pages.
SmashBox Limitless Lash Mascara, date published May 2003 wwww.gnpd.com, 2 pages.
Swab Plus Eye Makeup Remover Swabs, date published Nov. 2007; wwww.gnpd.com, 2 pages.
SwabPlus Waterproof Mascara Remover Swabs, date published Dec. 2002; wwww.gnpd.com, 2 pages.
Tarte Cosmetics, Tarte Fall 2008, Eye Couture Day-to-Night Eye Palette, date published Aug. 2008; www.gnpd.com, 2 pages.
The Art of Makeup, Vip Complete Cosmetic Kit, date published Feb. 2008; www.gnpd.com 4 pages.
Narus Cosmetics, Wink Up Mascara Remover, date published Mar. 1999; wwww.gnpd.com, 1 page.
Xtreme Color, Mary-Kate and Ashley, Eye Drama Creme Eye Color Plus Rich Mascara, date published Jul 2004; wwww.gnpd.com, 2 pages.
Yves Saint Laurent; Yves Saint Laurent Parfums; Duo Expert Sourcils, date published Nov. 2004; www.gnpd.com, 1 page.
PCT International Search Report and Written Opinion for PCT/US2013/041135 dated Nov. 8, 2013.
PCT International Search Report and Written Opinion for PCT/US2010/054090 dated Feb. 16, 2012.
PCT International Search Report and Written Opinion for PCT/US2010/054089 dated Feb. 16, 2012.
PCT International Search Report and Written Opinion for PCT/US2010/054085 dated Feb. 23, 2012.
PCT International Search Report and Written Opinion for PCT/IB2008/050102 dated Jun. 9, 2008.
PCT International Search Report and Written Opinion for PCT/US2010/054079 dated Feb. 23, 2012.
PCT International Search Report and Written Opinion for PCT/US2011/033429 dated Jun. 1, 2011.
PCT International Search Report and Written Opinion for PCT/US2011/057104 dated Feb. 21, 2012.
R.E. Lobnig et al., "Development of a new experimental method to determine critical pigment-volume-concentrations using impedance spectroscopy", Progress in Organic Coatings 55 (2006) 363-374.
J. Jachowicz et al., "The effect of the amphiprotic nature of human hair keratin on the adsorption of high charge density cationic polyelectrolytes", Colloid and Polymer Science 263: 847-858 (1985).
S.H.M. Gibson et al., "Determination of the critical pigment volume contrations of pigmented film coating formulations using gloss measurement", International Journal of Pharmaceutics 45, (1988) 245-248.
F. Zulli et al., "Preparation and properties of small nano particles for skin and hair care", SOFW Journal 123, Jahrgang 13/97 p. 880-885.
Masaki Okazaki et al., "Introduction of cationic groups onto carbon black surface and their.dispersibility in water", J. Dispersion Science and Technology 21(5), 511-524 (2000).

\* cited by examiner

SEMI-PERMANENT COSMETIC CONCEALER

CROSS REFERENCE TO RELATED APPLICATIONS

This application is a continuation-in-part of U.S. Ser. No. 13/274,852, filed on Oct. 17, 2011, which claims the benefit of U.S. Provisional Application No. 61/455,843, filed Oct. 27, 2010, and a continuation-in-part of U.S. Ser. No. 12/912,478, filed on Oct. 26, 2010, which claims the benefit of U.S. Provisional Application No. 61/255,457, filed Oct. 27, 2009.

FIELD OF THE INVENTION

Disclosed generally herein are semi-permanent concealer compositions for concealing undesirable blemishes, discolorations and/or other perceived cosmetic defects on skin and methods of use. In particular, disclosed herein is a long-wear concealer that can remain intact on the skin for more than 24 hours.

BACKGROUND OF THE INVENTION

Cosmetic compositions such as foundations and concealers have long been used to hide perceived imperfections of the skin and/or to improve the aesthetic appearance of a user. Foundations are generally intended to be applied to a person's face to create an even, uniform complexion and/or to change the skin tone, whereas concealers are commonly applied to a variety of different areas of the body (e.g., neck, hands, arms, legs, and torso). Thus, foundations and concealers often have different formulation requirements. For example, concealers are generally known to be more heavily pigmented than foundations.

Conventional cosmetic foundations are typically sold in a liquid, semi-liquid or cream, or powder form. The powder variety may include ingredients such as colorants (e.g., pigments, dyes, and lakes), bulking agents, binders, actives and other optional ingredients. Powder type foundations may be less complex to manufacture and may avoid some of the drawbacks of liquid foundations with regard to how they feel when applied and/or worn. But powder-type foundations may be perceived as having a shorter useful life than the liquid-type foundations (i.e., do not provide the desired cosmetic benefit for as long) and/or are more susceptible to undesirable transfer from the skin to another surface. This is due to the fact that powder-type foundation products are essentially individual solid particles lying on the skin surface with little to prevent them from being rubbed or wiped away.

Liquid-type and semi-liquid-type (e.g., creamy compact and solid emulsion) foundations may include ingredients such as tackifiers, colorants, rheology modifiers, solidifiers, surfactants, and actives disposed in a suitable carrier fluid. The carrier fluid of a liquid- or semi-liquid-type foundation typically includes a substantial amount of volatile components that evaporate from the skin during and shortly after application. It is not uncommon for conventional liquid and semi-liquid foundations to include more than 40% by weight of volatile components. After the foundation is applied to the face, the volatile components evaporate leaving the solid particles (including pigments, waxes, binders, tackifiers) distributed on the surface of the skin. To help bind the individual particles to the surface of the skin, "film-formers" are sometimes added to the foundation composition. When present at high enough levels, certain film-formers can form a continuous film on the skin, resulting in an undesirable dry and/or tight feeling. Thus, film-formers are generally included in conventional foundations at low levels (<10 wt %) to minimize any undesirable feel characteristics related to the use of the film-formers.

Conventional liquid or semi-liquid foundation compositions may also include non-volatile fluids (e.g., hydrocarbon oil, silicone oil, polyols), which help to provide a suitable fluid matrix into which some or all of the other ingredients in the foundation can be mixed. However, the non-volatile carrier fluids may cause the foundation to have a "greasy" feel when applied and/or worn, which some users may find to be particularly undesirable on their face. In order to provide a more desirable feel when the foundation is applied and/or worn, liquid foundations may be formulated as emulsions (e.g., water-in-oil or oil-in-water). The aqueous phase of the emulsion helps reduce the oily feel when the foundation is applied and/or worn. While the emulsion may improve the feel characteristics of the foundation, making an emulsion may also require additional equipment and/or process steps as compared to a single phase composition, which can increase the overall manufacturing cost and complexity. In addition, emulsions are commonly stabilized by using amphiphilic molecules (emulsifiers, surfactants). But the amphiphilic material provides the foundation with the ability to be chemically compatible with both hydrophobic and hydrophilic fluids (e.g. water, oil, sebum), which may reduce the useful lifespan of the foundation. Throughout the course of the day, the foundation is exposed to sebum (produced by the skin), moisture (sweat, tears, humidity, rain, washing) and oils (skin care products, other cosmetic products). As such, conventional liquid and semi-liquid foundations are not suited for staying on the skin for longer than 1 day.

Conventional concealers may include some of the same ingredients as foundations, but they are generally recognized as providing different cosmetic benefits and are intended to be used for different purposes. In particular, concealers are intended to be applied to a relatively small area of skin that has a particularly undesirable blemish (e.g., dark circles under the eyes, bruises, moles, hyper-/hypo-pigmented areas of the skin, scars, tattoos). Thus, concealers typically include higher pigment levels than foundations to help ensure sufficient coverage of the unsightly blemish. In addition, since a concealer is typically only applied to small areas of skin as opposed to being applied to the entire face, a level of formulation flexibility may available for a concealer that is unavailable for liquid foundations. For example, there may be more opportunity to formulate a concealer as a single phase composition. Further, it may be possible to include ingredients in a concealer that undesirably impact the way the concealer feels when applied and/or worn (e.g., ingredients that make the concealer harder to spread or add tackiness), which would be unacceptable in a foundation. Additionally it is possible to utilize much higher percentages of materials like tackifiers or film-formers that create a continuous film on the skin since the tight feeling they can cause is not a concern when applied to small surface areas.

One drawback shared by conventional concealers and foundations is that they may be unintentionally transferred to other surfaces (e.g., clothes, furniture, hair, and other areas of the body). Such transfers may result in clothing, furniture or other surfaces being soiled with makeup, and/or it may the effective life of the makeup. A variety of mechanisms may contribute to the undesired transfer of makeup from the skin. For example, sebum or other waxy/oily substances found on the skin can impede the ability of a foundation or concealer to adhere to the skin. In some instances, rubbing against a surface may abrade the concealer or foundation from the skin.

Regardless of the mechanism of transfer, the possibility that it will occur may cause some consumers to avoid purchasing and/or using cosmetic foundations altogether. The reduced effective life of a cosmetic product may be especially problematic for a user of a concealer, since the blemish(es) covered by the concealer are often perceived as being particularly unsightly.

In order to overcome the drawback of undesirable transfer and/or to increase the effective life of a concealer or foundation, "long-wear" or "transfer-free" products are known. However, even conventional long-wear or transfer-free products may not provide a suitable level of coverage and/or beauty enhancement for more than 24 hours or provide suitable resistance to the abrasion encountered by skin during typical daily activities. For example, it is well known that many women shave their legs, but a conventional concealer that is applied to legs may not provide a suitable level of cosmetic benefit following a shaving event. Similarly, a conventional concealer applied to the under-eye area (e.g., to hide dark or discolored areas) may not provide sufficient coverage for more than 24 hours due to the relatively high amount of sebum found on the face of a person and/or the increased amount of contact due to, for example, rubbing, scratching, and donning and removing glasses.

Formulators have attempted to improve the wear and longevity drawbacks of conventional concealers by including a tackifier in the composition. Tackifiers are generally recognized as chemical compounds commonly used in formulating adhesives to increase the tack or stickiness of the surface of the adhesive. While the addition of a tackifier may improve the resistance of a concealer or foundation to sebum or abrasion, it may also undesirably impact its feel. Adding a tackifier to a formulation tends to impart tackiness or stickiness to the composition, which users may find undesirable during application and/or wear. For example, a foundation that includes a tackifier may be difficult to spread on the face. In some instances, the increased tackiness of a foundation or concealer may cause debris (e.g., dust, dirt or similar contaminants) to stick to the skin surface where the makeup is present, which is typically undesirable. While makeup contamination is generally undesirable, it may be even more problematic for a foundation since it is applied to the entire face.

It is well known that some people simply do not like their skin to feel sticky, especially the skin on or around their face. Since concealers are sometimes used to cover blemishes on the face (e.g., under-eye area, age spot), tackifiers still be need to be used judiciously to help avoid negative perceptions of the concealer by consumers. Thus, even when tackifiers are added to conventional concealers, they are typically only present at a level of less than 15%, and even more typically at from 3-7%. Adding the tackifier at such relatively low levels may reduce stickiness, but it also limits the amount of resistance to sebum and abrasion that the tackifier is able to provide.

Accordingly, it would be desirable to provide a concealer product that can withstand the environmental insults typically faced by such a product when in use for more than twenty-four hours. It would also be desirable to provide a concealer or foundation that exhibits good abrasion resistance. It would further be desirable to provide a semi-permanent concealer product in the form of an anhydrous dispersion.

SUMMARY OF THE INVENTION

In order to provide a solution to the problems above, disclosed herein is a semi-permanent concealer comprising from about 10% to about 80% of a non-aqueous carrier; from about 15% to about 35% of a film-former comprising a tall oil glyceride; and from about 0.1% to about 20%, by weight, of colorant particles. The film-former and the particles are dispersed in the carrier to form an anhydrous dispersion, and the weight ratio of film-former to particles in the anhydrous dispersion is from about 2:3 to about 100:1.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

DETAILED DESCRIPTION OF THE INVENTION

All formulation/ingredient percentages are by weight, based on the weight of the composition, unless otherwise specified. All ratios are weight ratios, unless specifically stated otherwise. All numeric ranges are inclusive of narrower ranges; delineated upper and lower range limits are interchangeable to create further ranges not explicitly delineated. The number of significant digits conveys neither limitation on the indicated amounts nor on the accuracy of the measurements. All measurements are understood to be made at 25° C. and at ambient conditions, unless indicated otherwise, where "ambient conditions" means conditions under one atmosphere of pressure and at 50% relative humidity.

"Anhydrous" when used in conjunction with a cosmetic composition described herein means the composition includes less than 1% water (e.g., 0.5% or even 0%).

"Concealer" and "concealer composition," as used herein, mean a cosmetic composition that is applied to skin to hide a perceived imperfection (e.g., discoloration such as hyper pigmentation (e.g., age spot, mole, freckle and the like), scar, tattoo, fine line, wrinkle, and vascularization). In some instances, concealers may be applied to relatively small areas of the face (e.g., under-eye area) but are not intended to be applied to the entire face. This feature distinguishes concealers from foundations, which are intended to be applied to the entire face of a person. "Dried" when referring to a film means that the film is substantially free of volatile liquids.

"Hyper-pigmentation" and variations thereof mean an area of skin that appears darker than the natural tone of the surrounding skin (i.e., without makeup) due to an increase in melanin production. Nonlimiting examples of hyper-pigmentation include freckles, moles, birthmarks, solar lentigines (age spots or liver spots), melasma or chloasma.

Hypo-pigmentation and variations thereof mean an area of skin that appears lighter than the natural tone of the surrounding skin due to a decrease in melanin production.

"Keratinous tissue," as used herein, refers to keratin-containing layers disposed as the outermost protective covering of mammals which includes, but is not limited to, skin, hair, and nails.

Semi-Permanent Concealer Formula

Disclosed herein is a semi-permanent concealer formula that remains intact on a target skin surface for greater than 24 hours (e.g., greater than 36 hours, greater than 48 hours, or even up to 120 hours). The novel semi-permanent concealer formula achieves a multiple day wear benefit through two formula design elements. The first element is the film-former. Tackifiers are generally not recognized as being film-formers suitable for use in cosmetic products. But it has been surprisingly found that certain tackifiers may provide suitable film-forming characteristics for use herein. Tackifiers are generally recognized as low molecular weight compounds commonly added to adhesive polymer systems (e.g., hot melt-type adhesives or pressure-sensitive adhesive systems that also include a higher molecular weight polymer) to increase adhesion. The tackifier is generally added at relatively low amounts (e.g., less than 5%) because of its low molecular weight (i.e., viscosity) and high tackiness. If included at a high level or without a suitable polymer, the tackifier may cause the adhesive to have an undesirably low viscosity (which can increase "bleed-through") and/or an increased risk of contamination (e.g., to manufacturing equipment or other portions of the article or substrate). However, not all tackifiers can form a film that has suitable film flexibility, abrasion resistance, and water and surfactant resistance when incorporated into a concealer. This is especially true for tackifiers that are added at a high level, such as in the present concealer. The rosinate materials described herein have been found to provide a particularly suitable combination of the desired properties when incorporated into the present concealer at high levels.

The second element important for providing the present semi-permanent concealer is balancing the ratio of film-former to other non-volatile components in the concealer formula such that there is sufficient film-former to form a continuous phase. In particular, it is important to balance the ratio of film-former to particles in the composition. The paint industry has recognized that the properties of a film are directly related to the volume concentration of solids it contains since the introduction of the concept of critical pigment volume concentration (CPVC) in 1949 by Asbeck and Van Loo. The CPVC is the point at which there is just sufficient film-former matrix to wet and fill the voids between individual particles. At volume concentrations above the CPVC, the film-former matrix is no longer a continuous phase. Decreasing the particle size of the solids increases the CPVC for a given system. Studies have shown that the pigment volume concentration impacts many film properties, including film flexibility and abrasion resistance. As the pigment volume concentration increases, film flexibility decreases and abrasion resistance remains the same or improves. When the CPVC is exceeded, the film will become brittle and abrasion resistance will decrease rapidly.

Conventional concealer formulations use large amounts of waxes (5-15%) and iron oxides (6-12%) while using relatively small amounts of film-formers (4-8%). The films formed by such conventional concealers are dominated by the waxes which can have crystal sizes in excess of 20 microns and are jagged and rough in appearance. Because conventional concealers tend to include large particulates and a relatively low amount of film-former, they may have a solids volume concentration in excess of the CPVC. As a result, conventional concealer films exhibit poor abrasion resistance and often are very brittle films which flake very easily.

Figure 1:
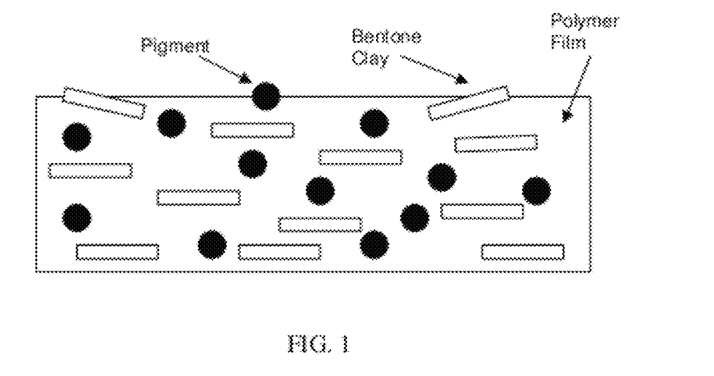
FIG. 1 illustrates a hypothesized film structure of the present semi-permanent concealer.
Figure 2:
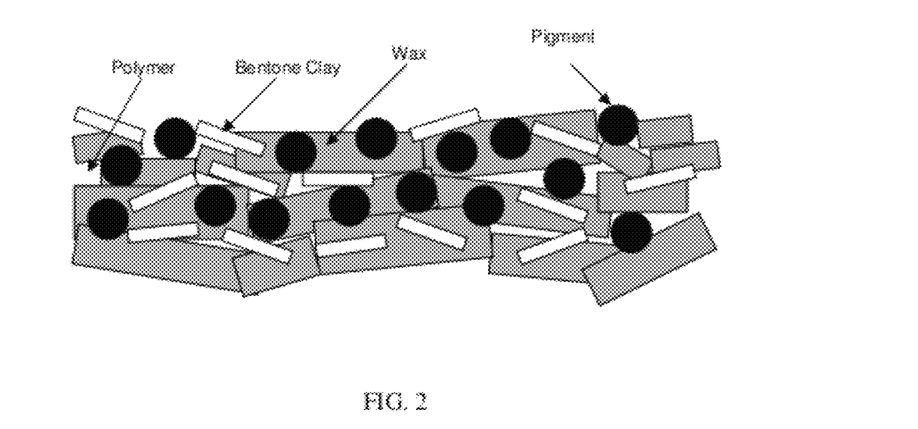
FIG. 2 illustrates a hypothesized film structure of a conventional concealer.

The present semi-permanent concealer has a volume concentration of solids that is below the CPVC. This is achieved in two ways. First, small particle size solids are selected for both the pigments and thickeners. In some instances, for example, the present concealer may be thickened using only disteardimonium hectorite clay particles (D90<10 microns) from 10% to 15% by weight of the composition, and colored with iron oxides, titanium dioxide, micas (D90<30 micron) from 7% to 10% by weight of the composition. Minimizing the size of the particulates in the system increases the CPVC for the present concealer relative to that of conventional concealers. Second, a greater level of film-former is used e.g., 15-30% or 17-25%) which ensures that the concentration of solids in the present concealer is below the CPVC. Because its solids volume concentration is below the CPVC, it has improved resistance to flaking and transfer caused by stretching and abrading relative to conventional concealers. Suitable ratios of film-former to particles in the present concealer include from 2:3 to 100: (e.g., 1:1-50:1, 1:2-30:1, or 1:3-20:1). The hypothesized film structure of the new semi-permanent concealer is shown in FIG. 1. The hypothesized film structure of a conventional concealer formula technology is shown in FIG. 2.

The present semi-permanent concealer may be provided in the form of a single-phase, anhydrous dispersion comprising colorant particles dispersed in a matrix of film-former(s) and volatile solvent(s). The single-phase, anhydrous dispersion provides several desirable characteristics compared to conventional emulsions. For example, the single-phase dispersion does not require the addition manufacturing equipment or process steps needs to form an emulsion. And the lack of an aqueous phase to interact with the incompatible oils naturally found on skin may improve the adhesion properties of the concealer. In some instances, the new semi-permanent formula may include isododecane as a volatile carrier, a combination of rosinate film-formers, and one or more iron oxides as colorants. The matrix may be stabilized using a clay network. Individual ingredients suitable for use with the present semi-permanent concealer are described in more detail below.

Carrier Solvents

The semi-permanent concealer composition herein may include a carrier solvent to achieve delivery of the film-former and other formula components to a target skin surface. The carrier solvent may include an oil such as, for example, a volatile oil, non-volatile oil, a polar oil, a non-polar oil or a mixture of these. "Non-volatile" when employed in relation to an oil herein means an oil that fulfills at least one of the following definitions: (a) the oil exhibits a vapor pressure of no more than 0.2 mm Hg at 25° C. and one atmosphere pressure; or (b) the oil has a boiling point at one atmosphere of at least 300° C. "Relatively polar" means a first oil is more polar than a second oil in terms of solubility parameter (i.e., the higher the solubility parameter the more polar the oil). "Non-polar" means that the oil has a solubility parameter below about 6.5 $(cal/cm^3)^{0.5}$. The present concealer composition may include from 1% to 80%, from 10% to 70%, or even from 15% to 65% of an oil. Optionally, the cosmetic composition may include from 0.1% to 20% or from 1 to 10% by weight of a non-volatile oil. Suitable, non-limiting examples of oils are discussed in more detail below.

Non-polar, Volatile Oils

In certain embodiment, the semi-permanent concealer composition may include a volatile carrier which quickly volatilizes from the target skin surface, leaving the desired components behind. The non-polar, volatile oil may be included to help provide desirable aesthetic properties to the present concealer (e.g., good spreadability, non-greasy and/or tacky feel, quick drying to allow pigment particles to set on skin). The volatile carrier may be present at an amount of from 10% to 85%, from 15% to 80%, or from 20% to 70% by weight. Non-polar, volatile oils suitable for use herein include silicone oils, hydrocarbons, and mixtures thereof. The non-polar, volatile oils may be either saturated or unsaturated, have an aliphatic character and be straight or branched chains or even contain alicyclic or aromatic rings. Examples of suitable non-polar, volatile hydrocarbons for use herein include without limitation those having boiling points in the range of 60-260° C. and/or having from $C_7$ to $C_{20}$ chain lengths (e.g., $C_8$-$C_{15}$). Particularly suitable examples of volatile hydrocarbons include $C_8$-$C_{20}$ isoparaffins such as isododecane, isohexadecane, isoeicosane, 2,2,4-trimethylpentane, 2,3-dimethylhexane and mixtures thereof. Commercially available volatile hydrocarbons suitable for use herein include Permethyl 99A available from Presperse; Parafol 12-97 and Parafol 14 both available from Sasol; and the Isopar Series available from Exxon Chemicals.

Suitable volatile silicone fluids include without limitation cyclomethicones having 3, 4 and 5 membered ring structures corresponding to the formula:

wherein n=3 to 7; and linear volatile silicones corresponding to the formula:

wherein m=1 to 7.

Linear volatile silicone oils typically have a viscosity of less than 5 centistokes at 25° C., whereas the cyclic silicones typically have a viscosity of less than 10 centistokes at 25° C. Examples of suitable volatile silicone oils include cyclomethicones of varying viscosities, e.g., Dow Corning 200, 244, 245, 344 and 345 all available from the Dow Corning Corp.; SF-1204 and SF-1202 Silicone Fluids available from G.E. Silicones, GE 7207 and GE 7158 available from General Electric Co.; and SWS-03314 available from SWS Silicones Corp. In addition, Caprylyl Methicone such as DC FZ3196, which is available from Dow Corning, may be used in certain embodiments.

Relatively Polar, Non-Volatile Oils

This non-volatile oil is "relatively polar" compared to the non-polar, volatile oil discussed above. Relatively polar, non-volatile oils potentially suitable for use herein are disclosed, for example, in Cosmetics, Science, and Technology, Vol. 1, 27-104 edited by Balsam and Sagarin, 1972; U.S. Pat. No. 4,202,879 issued to Shelton on May 13, 1980; and U.S. Pat. No. 4,816,261, issued to Luebbe et al. on Mar. 28, 1989. Nonlimiting examples of relatively polar, non-volatile oils include silicone oils; hydrocarbon oils; fatty alcohols; fatty acids; esters of mono and dibasic carboxylic acids with mono and polyhydric alcohols; polyoxyethylenes; polyoxypropylenes; mixtures of polyoxyethylene and polyoxypropylene ethers of fatty alcohols; and mixtures thereof. The relatively polar, non-volatile oils may be saturated or unsaturated, linear or branched, aromatic or aliphatic, and/or contain one or more ring structures. For example, fatty alcohols having from about 12-26 carbon atoms; fatty acids having from about 12-26 carbon atoms; esters of monobasic carboxylic acids and alcohols having from about 14-30 carbon atoms; esters of dibasic carboxylic acids and alcohols having from about 10-30 carbon atoms; esters of polyhydric alcohols and carboxylic acids having from about 5-26 carbon atoms; ethoxylated, propoxylated, and mixtures of ethoxylated and propoxylated ethers of fatty alcohols with from about 12-26 carbon atoms and a degree of ethoxylation and propoxylation of below about 50; and mixtures thereof are suitable. Other suitable examples include propoxylated ethers of C14-C18 fatty alcohols having a degree of propoxylation below about 50; esters of C2-C8 alcohols and C12-C26 carboxylic acids (e.g. ethyl myristate, isopropyl palmitate); esters of C12-C26 alcohols and benzoic acid (e.g. Finsolv TN supplied by Finetex); diesters of C2-C8 alcohols and adipic, sebacic, and phthalic acids (e.g., diisopropyl sebacate, diisopropyl adipate, di-n-butyl phthalate); polyhydric alcohol esters of C6-C26 carboxylic acids (e.g., propylene glycol dicaprate/dicaprylate, propylene glycol isostearate); and mixtures thereof; branched-chain aliphatic fatty alcohols having from about 12-26 carbon atoms; isocetyl alcohol; octyldecanol; octyldodecanol; and undecylpentadecanol; and octyldodecanol. Aliphatic fatty alcohols such as those disclosed herein may be particularly useful in combination with the volatile liquid silicone oils discussed herein to adjust the average solubility of the solvent. In addition, materials such as diethylhexyl carbonate (such as Tegosoft DEC from Evonik) can be used.

Non-Polar, Non-Volatile Oils

The carrier solvent may include non-volatile, non-polar oils. When included in the present concealer, the non-volatile, non-polar oil may act as an emollient, for example, as disclosed in U.S. Pat. No. 4,202,879 issued to Shelton on May 13, 1980 and U.S. Pat. No. 4,816,261 issued to Luebbe et al. on Mar. 28, 1989. Nonlimiting examples of non-volatile oils suitable for use herein include non-volatile polysiloxanes, paraffinic hydrocarbon oils, and mixtures thereof. Suitable nonlimiting examples of polysiloxanes have a viscosity of from 1 to 100,000 centistokes at 25° C., and include polyalkylsiloxanes (e.g., polydimethyl siloxanes such as Viscasil® series available from the General Electric Company and the Dow Corning 200 series available from Dow Corning Corp.), polyarylsiloxanes, polyalkylarylsiloxanes (e.g., polymethylphenyl siloxanes that have a viscosity of from 15 to 65 centistokes at 25° C., such as SF 1075 methyl-phenyl fluid available from the General Electric Company and 556 Cosmetic Grade Fluid available from Dow Corning Corp.), polyethersiloxane copolymers (e.g., a polyoxyalkylene ether copolymer having a viscosity of about 1200 to 1500 centistokes at 25° C., such as SF1066 organosilicone surfactant available from the General Electric Company). A particularly suitable poly-ethersiloxane copolymer is polysiloxane ethylene glycol ether copolymer.

Non-volatile paraffinic hydrocarbon oils useful herein are mineral oils and certain branched-chain hydrocarbons. Examples of these fluids are disclosed in U.S. Pat. No. 5,019,375 issued to Tanner et al. on May 28, 1991. Particularly suitable branched-chain hydrocarbons include Permethyl 103 A, which contains an average of about 24 carbon atoms; Permethyl 104A, which contains an average of about 68 carbon atoms; Permethyl 102A, which contains an average of about 20 carbon atoms; all of which are available from Permethyl Corporation; and Ethylflo 364 which contains a mixture of 30 carbon atoms and 40 carbon atoms available from Ethyl Corp. When used herein, volatile or non-volatile hydrocarbon oils may be present at concentrations of less than 30% (e.g., from 1% to 25% or from 1% to 15%).

Film-former

An essential component of the present concealer is a film-former selected from a class of rosinates or rosin esters. In some instances, the semi-permanent concealer composition may include a film-former chosen from the group consisting of tall oil glycerides, pentaerythrityl rosinate, glyceryl rosinate, and mixtures thereof, wherein the tall oil glycerides and pentaerythrityl rosinates are particularly suitable. These materials are derived from rosin, which is a solid form of resin obtained from conifers. Rosin may be produced by heating liquid resin to vaporize the volatile liquid terpene components. Rosin primarily consists of different resin acids, especially abietic acid. Rosin is commercially available and is commonly produced by distillation of volatile turpentine from oleoresin exuded from the wound of living pine trees to obtain gum rosin or by separating tall oil, a byproduct of the wood pulp industry, to obtain tall oil rosin. The carboxylic acid group of a rosin acid can be converted to an ester through a reaction with various alcohols. Esterification of rosin modifies the softening point, adhesiveness, cohesiveness, and melted viscosity of the material. The alcohols typically used to make rosin esters are methanol, tri-ethylene-glycol, glycerol, and pentaerythritol. Tall oil rosin is esterified with glycerol to form tall oil glycerides, a mixture of resin acids, rosin acids, and esters of glycerol. Tall oil glycerides are available from, for example, Arizona Chemical Co. Glyceryl rosinate, is the ester of rosin acids with glycerol. Pentaerythrityl rosinate, sometimes referred to as pentaerythritol rosinate, is the ester of rosin acids with pentaerythritol, and may be included as a skin conditioning agent (i.e., emollient) and/or as a non-aqueous, viscosity-increasing agent. Pentaterythrityl rosinate is commercially available, for example, from Eastman.

The conjugated double bond present in rosin makes it susceptible to oxidation, isomerization and other reactions. A common method to improve stability is to hydrogenate the rosin molecules. This is done by the addition of hydrogen to double bonds in the resin acid, typically catalyzed by nickel compounds or noble metals to form saturated ring structures. Hydrogenation greatly increases the molecule's resistance to oxidation and improves its color. The hydrogenation process can be controlled so that the rosin is either partially or fully hydrogenated. Hydrogenated rosins have specific advantages over non-hydrogenated rosin resins including lighter color, improved stability, and reduced skin sensitization. The hydrogenated versions of pentaerythrityl rosinate and glyceryl rosinate, pentaerythrityl hydrogenated rosinate (PHR) and glyceryl hydrogenated rosinate (GHR) may be used in the invention.

Tackifiers such as tall oil glycerides, pentaerythrityl rosinate, pentaerythrityl hydrogenated rosinate, glyceryl rosinate, and glyceryl hydrogenated rosinate may used in the present concealer in higher concentration than previously used in conventional concealers. As mentioned above, tackifiers are typically not included in conventional concealers at high levels due to, for example, the undesirable tackiness that they cause and poor film-forming characteristics. However, the present semi-permanent concealer formula may include tackifiers such as those described above at 15% or more (e.g., at least 17%, at least 20%, and up to between 30% and 35%) without imparting an undesirable amount of tackiness to the concealer and/or exhibiting undesirable film-forming characteristics. The ratio of film-former to volatile carrier is controlled such that the dried film consists of from 30% to 70% film-former by weight, preferably from 40% to 60%, and most preferably 50%.

Colorants

Colorants may be included in the present concealer to provide a variety of different colors and shades to match the desired skin color and/or tone of an individual user. For example, the concealer may be colored such that it has an L-value of between 76 and 50 on the L*C*h color scale. Colorants suitable for use in the present concealer include without limitation conventional dyes, pigments, lakes, and mixtures thereof (e.g., organic or inorganic pigments or colorants approved for use in cosmetics that are applied to the skin by the CTFA and/or the FDA). Examples of colorants include without limitation inorganic pigments such as chromium oxides, chromium hydroxide, bismuth oxychloride, zinc oxide, ultramarines, iron oxides (e.g., yellow, brown, red), mica, ferric ammonium ferrocyanide, ferric ferrocyanide, manganese violet, aluminum powder, bronze powder, copper powder and titanium oxide; organic pigments such as D&C Black No. 2, D&C Black No. 3, FD&C Red No. 40, D&C Green No. 5, FD&C Blue No. 1, and FD&C Yellow No. 5; Pigmentary-grade metal oxide particles may be particularly suitable colorants for use herein to provide coverage and colour to the skin. Suitable pigmentary-grade iron oxide particles may have an average primary particle size greater than 100 nm (e.g., from 100 nm to 500 nm). pigmentary-grade iron oxide particles by weight of the total composition. The present semi-permanent concealer composition may include from 0.05 to 70% (e.g., 0.05 to 50 wt %, 0.1 to 35 wt %, 0.5% to 15%, 1% to 12%, or even 5% to 10%) of a colorant. Colorants having average diameters of 0.1 to 10 microns (e.g., 0.1 to 5 or even 0.1 to 1 microns) may be suitable for use herein. It may be desirable to select colorants with a diameter that is less than the thickness of the concealer composition dried-down film (e.g., less than 40 microns), which allows the colorant particles to be fully encased in the dried film.

Pigment particles, if used herein, may be surface modified with a hydrophobic coating such as, for example, triethoxycaprylsilane, methicone, or dimethincone, which is commonly known. Pigment particles such as iron oxides, mica, and titanium oxide tend to have a hydrophilic surface that contains polar hydroxyl groups. The polar hydroxyl groups adsorb moisture which can result in poor dispersibility characteristics when included in a non-aqueous dispersion. Thus, hydrophobically coating the pigments particles may increase the dispensability of the colorant in a non-polar solvent and increase the resistance of the colorant to being washed off, for example, during showering.

In certain embodiments, the present concealer may include iron containing titanium dioxide particles that serve to reduce blue reflectance from skin, as disclosed in US. Publication Nos. 2010/0074928, 2010/0003205 and 2010/0003293, all filed by Elliot, et al., on Jul. 1, 2009. Suitable iron containing titanium dioxide pigments are available from Ishihara Sangyo Kaisha Ltd under the trade name FX50, or Nikko Rica Corporation under the trade name Fincera®. The iron containing titanium dioxide may be present at from 0.05% to 20%, from 1% to 15%, from 2% to 12.5%, or even from 3% to 10%. The proportion of these particles may vary depending on the desired level of coverage and/or shade of the product. For example, to minimise shininess when the cosmetic composition is expected to be used on darker skin, it may be desirable that the composition include a relatively high proportion of iron-containing titanium dioxide particles, for example from 5% to 10% by weight of such particles based on the weight of the cosmetic composition.

The present concealer may include non-pigmentary-grade, transparent iron oxide particles (i.e., iron oxide particles that have an average primary particle size of less than or equal to 100 nm when measured by transmission electron microscopy). The transparent iron oxide particles may have an average surface area of from 30 $m^2/g$ to 150 $m^2/g$ (e.g., from 50 $m^2/g$ to 150 $m^2/g$, or from 60 $m^2/g$ to 150 $m^2/g$). The transparent iron oxide particles may be selected from transparent yellow iron oxide particles, transparent red iron oxide particles, transparent black iron oxide particles, and mixture thereof. Examples of commercially available transparent iron oxide particles include FAF40TRR, FAF40TRY, CM3F30TRR, CM3F40TRR, CM3F30TRY and CM3F40TRY supplied by Kobo; Trionix® materials from Noviant; and, the SunChroma® materials from Sun Chemicals. The present concealer may include from 0.05% to 10%, from 0.1% to 5%, or even from 0.1% to 4%, transparent iron oxide particles.

In certain embodiments, it may be desirable to include encapsulated colorant microparticles having average diameters of from 0.1 to 10 microns (e.g., from 0.1 to 5 microns or from 0.1 to 1 micron) in the present concealer. The encapsulated colorant microparticles may comprise 1 to 60% by weight of at least one organic colorant (e.g., 5-40 wt % or 7-25 wt %). The microencapsulated colorants may provide a suitably vibrant color to products used on the skin if desired. And microparticles can be made without the milling or grinding typically needed to make conventional non-encapsulated colorants.

Optional Ingredients

The semi-permanent concealer composition may optionally include a variety of additional ingredients, as desired. Since the present concealer is provided in the form of a non-aqueous dispersion it may be desirable to select optional ingredients that can be suitable dispersed in a non-polar carrier. Nonlimiting examples of various optional ingredients that may be included herein, such as thickeners, particles, elastomers, actives, sunscreen agents, preservatives, skin conditioning agents, solidifying agents, preservatives and fragrances, are discussed in more detail below.

Thickeners

The semi-permanent concealer composition may optionally be thickened or structured with colloidal particles such as disteardimonium hectorite, kaolin, silica, and magnesium carbonate; viscous hydrocarbons; and combinations thereof. Disteardimonium hectorite is the preferred thickener to build structure/viscosity. This may help to provide proper spreading/deposition across a target skin surface and adequate stability/suspension of colorant particles in the dispersion over time. It may be desirable to select disteardimonium hectorite particles that have a diameter that is less than the thickness of the concealer dried-down film, (e.g., less than 40 microns). In certain embodiments, the concealer composition may include disteardimonium hectorite in an amount of from 1% to 25%, 2% to 20%, or even 3% to 15%.

In certain embodiments, the present concealer composition may be thickened with one or more wax(es) such as, for example, carnauba wax, candellila wax, beeswax, and polyethylene wax. However, it is important not to include too much wax as it may undesirably reduce the abrasion resistance of the concealer. In certain embodiments, the semi-permanent concealer composition may include less than 3.0%, less than 1.0%, or even less than 0.1% of wax and/or wax like components. In certain embodiments, the semi-permanent concealer composition may be free of wax.

Particles

The present concealer may optionally include one or more particles for modifying the application and appearance of the film formed by the tackifier. For example, particles may be included in the cosmetic composition to help minimize the undesirable tacky sensation of sunscreen actives and film-forming tackifiers on a user's hands as well as helping to "mattify" the film and extend the wear of the concealer. In certain embodiments, at least some of the particles may be in the form of one or more of the pigments described above. The particles may help provide even coverage during application of the concealer.

Particles may be added to extend the wear of the concealer film by absorbing components of sebum and sweat, thereby limiting the mobility of the concealer film across skin. The amount of particles present is important because too few particles may result in a cosmetic composition that exhibits an undesirable shine when applied to the skin. On the other hand, too many particles may cause the concealer to exhibit an undesirable chalky appearance when applied to the skin. In addition, it is believed without being limited by theory, that the type of particles present in the concealer is important for providing a desirable appearance on skin. In some instances, the particles may be selected such that the concealer has a suitable matte look. A matte look may be thought of as being the opposite of a shiny look, which is generally undesirable for certain cosmetic compositions such as foundations and concealers. A matte look may be generated when the surface topography of the foundation film is rough, thus increasing the amount of diffuse back-scatter of light from the surface of the foundation film. In some instances, the properties of the concealer (e.g., rough surface topography) may be manipulated by using particles such as Surface Topography Modifiers, Locking Oil Absorbers and/or Releasing Oil Absorbers. Nonlimiting examples of such particles and their use in cosmetic composition is disclosed in copending U.S. Ser. No. 13/274,852.

Elastomer

Elastomers may be optionally added to modify the skin feel of the concealer as well as its optical properties. In certain embodiments, the elastomer may include a cross-linked organopolysiloxane elastomer. The elastomer may be present at an amount of from 0.01% to 15%, from 1% to 12.5%, or even from 2% to 10%. Nonlimiting examples of elastomers include dimethicone/vinyl dimethicone crosspolymers such as DC 9040, DC 9045 and DC 9041 available from the Dow Corning Corporation; SFE 839 available from General Electric; KSG-15, KSG-16 and KSG-18 from Shin Etsu Chemical Company Ltd; and Gransil™ line of materials from Grant Industries, and lauryl dimethicone/vinyl dimethicone crosspolymers such as KSG-31, KSG-32, KSG-41, KSG-42, KSG-43, and KSG-44 available from Shin Etsu Chemical Company Ltd. Other exemplary elastomers include polyoxyalkylene-modified elastomers formed from divinyl compounds, particularly siloxane polymers with at least two free vinyl groups, reacting with Si—H linkages on a polysiloxane backbone, such as KSG-21, KSG-210 and KSG-320 available from the Shin-Etsu Chemical Company Ltd. Further examples of elastomers include cross-linked organopolysiloxane elastomers comprising polyglyceryl units such as KSG 710 and KSG-800 available from the Shin-Etsu Chemical Company Ltd.

Actives

The present concealer may optionally include a safe and effective amount of a biological, chemical, nutraceutical, or pharmaceutical active. Biological actives include prostaglandins, antimicrobials, antibacterials, biocides, preservatives, proteins, amino acids, peptides, hormones, growth factors, enzymes (e.g., glutathione sulphydryl oxidase, transglutaminase), therapeutics, oligonucleotides, genetic materials (e.g., DNA, RNA), and combinations thereof. Chemical actives include surfactants, sensates, hair conditioners, hair dyes, hair growth agents, hair removers, hair growth inhibitors, hair styling gels, and combinations thereof. Nutraceutical actives include proteins, preservatives, vitamins, food-additive materials, and combinations thereof. Pharmaceutical actives include antibiotics and other drugs. Particular suitable examples of actives are whitening actives (e.g., SEPIWHITE available from Seppic) and anti-acne actives such as benzoyl peroxide.

Sunscreen

The present concealer may optionally include a sunscreen agent. A sunscreen agent is an ingredient or composition that absorbs or reflects at least some of the sun's ultraviolet (UV)

radiation and is typically incorporated into a topical product for skin. Sunscreen agents can be organic or inorganic. The sunscreen agent may be present at an amount of from 0.1% to 16%, from 0.2% to 12%, or even from 0.5% to 8%. Nonlimiting examples of inorganic sunscreen agents include titanium dioxide and zinc oxide particles. Such metal oxide particles may have an average primary particle size equal to or less than 100 nm. These particles may be selected from sunscreen-grade titanium dioxide, sunscreen grade zinc oxide and mixtures thereof. These particles may be surface-treated and/or coated, using conventional treatments. Examples of commercially available sunscreen metal oxide particles include M262 from Kemira Corp., TTO S-3 and TTO S-4 from Ishihara Corp. Nonlimiting examples of organic sunscreen agents include cinnamate derivatives (e.g., ethylhexyl methoxycinnamate and ethyl methoxycinnamate); alkyl $\beta,\beta$-diphenylacrylate derivatives (e.g., ethyl 2-cyano-3,3-diphenylacrylate) and 2-ethylhexyl 2-cyano-3,3-diphenylacrylate); $\alpha$-cyano $\beta,\beta$-diphenylacrylate derivatives; anthranilate derivatives (e.g., methyl anthranilate); benzophenone derivatives (e.g., methyl benzophenone and trimethylbenzophenone); camphor derivatives (e.g., benzylidene camphor sulfonic acid); dibenzoylmethane derivatives (e.g., butyl methoxydibenzoylmethane, ethylhexyl methoxydibenzoylmethane, and isopropyl dibenzoylmethane); p-aminobenzoic derivatives (e.g., p-aminobenzoic acid butyl ester and p-aminobenzoic acid); salicylic derivatives, triazine derivatives (tris-biphenyl triazine); and mixtures thereof. A suitable example of a hydrophilic organic sunscreen agent is 2-phenylbenzimidaole-5-sulfonic acid, also known as PBSA.

Skin Conditioning Agent

The present concealer compositions may optionally include a skin conditioning agent (e.g., exfoliants and/or emollients) present at an amount of from 1% to 30%, from 2% to 20%, or even from 3% to 10% by weight based on the weight of the cosmetic composition. 1 to 15% or even 2 to 10%. Exemplary exfoliants include C2-C30 alpha-hydroxycarboxylic acids, beta-hydroxycarboxylic acids and salts of these acids. Nonlimiting examples of C2-C30 alpha-hydroxycarboxylic acids include alpha-hydroxyethanoic acid, alpha-hydroxypropanoic acid, alpha-hydroxyhexanoic acid, alpha-hydroxyoctanoic acid, alpha-hydroxydecanoic acid, alpha-hydroxydodecanoic acid, alpha-hydroxytetradecanoic acid, alpha-hydroxyhexadecanoic acid, alpha-hydroxyoctadecanoic acid, alpha-hydroxyeicosanoic acid, alpha-hydroxydocosanoic acid, alpha-hydroxyhexacosanoic acid, and alpha-hydroxyoctacosanoic acid. An example of a beta-hydroxycarboxylic acid exfoliant is salicylic acid.

When the conditioning agent is an emollient, it may be selected from hydrocarbons, fatty acids, fatty alcohols and esters. Isononyl isononanoate is a particularly suitable emollient conditioning agent. Other hydrocarbons that may be employed include mineral oil, polyolefins such as polydecene, and paraffins such as isohexadecane (e.g. Permethyl® 99 and Permethyl® 101). The present concealer may optionally be substantially free of semi-solid hydrocarbons such as petrolatum, lanolin and lanolin derivatives, sterols (e.g., ethoxylated soya sterols), high molecular weight polybutenes and coco butter. "Substantially free" means that the concentration of the semi-solid hydrocarbons are less than 10%, less than 5%, less than 2%, or even 0. Without being limited by theory, such semi-solid hydrocarbons may mask the sensory benefits of a siloxane elastomer, such as the non-greasy, light feel.

Fatty acid- and alcohol-type emollients may have from 10 to 30 carbon atoms. Nonlimiting examples of these include pelargonic, lauric, myristic, palmitic, stearic, isostearic, hydroxystearic, oleic, linoleic, ricinoleic, arachidic, behenic and erucic acids and alcohols.

Oily ester emollients may be those selected from one or more of the following classes: 1) Triglyceride esters such as vegetable and animal fats and oils (e.g., castor oil, cocoa butter, safflower oil, cottonseed oil, corn oil, olive oil, cod liver oil, almond oil, avocado oil, palm oil, sesame oil, squalene, Kikui oil and soybean oil); 2) Acetoglyceride esters such as acetylated monoglycerides; 3) Ethoxylated glycerides such as ethoxylated glyceryl monostearate; 4) Alkyl esters of fatty acids having 10 to 20 carbon atoms (e.g., hexyl laurate, isohexyl laurate, isohexyl palmitate, isopropyl palmitate, decyl oleate, isodecyl oleate, hexadecyl stearate, decyl stearate, isopropyl isostearate, diisopropyl adipate, diisohexyl adipate, dihexyldecyl adipate, diisopropyl sebacate, lauryl lactate, myristyl lactate, and cetyl lactate); 5) Alkenyl esters of fatty acids having 10 to 20 carbon atoms (e.g, oleyl myristate, oleyl stearate, and oleyl oleate); 6) Ether-esters such as fatty acid esters of ethoxylated fatty alcohols; 7) Polyhydric alcohol esters (e.g., ethylene glycol mono and di-fatty acid esters, diethylene glycol mono- and di-fatty acid esters, polyethylene glycol (200-6000) mono- and di-fatty acid esters, propylene glycol mono- and di-fatty acid esters, polypropylene glycol 2000 monooleate, polypropylene glycol 2000 monostearate, ethoxylated propylene glycol monostearate, glyceryl mono- and di-fatty acid esters, polyglycerol polyfatty esters, ethoxylated glyceryl monostearate, 1,2-butylene glycol monostearate, 1,2-butylene glycol distearate, polyoxyethylene polyol fatty acid ester, sorbitan fatty acid esters, and polyoxyethylene sorbitan fatty acid esters); 8) Wax esters such as beeswax, spermaceti, myristyl myristate, stearyl stearate; 9) C1-C30 mono- and poly-esters of sugars and related materials in liquid or solid form. Other materials include cottonseed oil or soybean oil fatty acid esters of sucrose. The ester materials are further described in U.S. Pat. Nos. 2,831,854, 4,005,196, to Jandacek, issued Jan. 25, 1977; U.S. Pat. No. 4,005,195, to Jandacek, issued Jan. 25, 1977, U.S. Pat. No. 5,306,516, to Letton et al., issued Apr. 26, 1994; U.S. Pat. No. 5,306,515, to Letton et al., issued Apr. 26, 1994; U.S. Pat. No. 5,305,514, to Letton et al., issued Apr. 26, 1994; U.S. Pat. No. 4,797,300, to Jandacek et al., issued Jan. 10, 1989; U.S. Pat. No. 3,963,699, to Rizzi et al, issued Jun. 15, 1976; U.S. Pat. No. 4,518,772, to Volpenhein, issued May 21, 1985; and U.S. Pat. No. 4,517,360, to Volpenhein, issued May 21, 1985.

Solidifying Agent

The cosmetic compositions of this invention can contain one or more materials, herein singly or collectively referred to as a "solidifying agent", that are effective to solidify the particular liquid base materials to be used in a cosmetic composition. (As used herein, the term "solidify" refers to the physical and/or chemical alteration of the liquid base material so as to form a solid or semi-solid at ambient conditions, i.e., to form a final composition which has a stable physical structure and is deposited on the skin during normal use conditions.) As is appreciated by those skilled in the art, the selection of the particular solidifying agent for use in the cosmetic compositions will depend upon the particular type of composition desired, i.e., gel or wax-based, the desired rheology, the liquid base material used and the other materials to be used in the composition. The solidifying agent is preferably present at a concentration of from about 0 to about 90%, more preferably from about 1 to about 50%, even more preferably from about 5% to about 40%, most preferably from about 1% to about 15%.

Suitable solidifying agents include waxy materials such as candelilla, carnauba waxes, beeswax, spermaceti, carnauba, baysberry, montan, ozokerite, ceresin, paraffin, synthetic waxes such as Fisher-Tropsch waxes, silicone waxes (e.g., DC 2503 from Dow Corning), microcrystalline waxes and the like; soaps, such as the sodium and potassium salts of higher fatty acids, i.e., acids having from 12 to 22 carbon atoms; amides of higher fatty acids; higher fatty acid amides of alkylolamines; dibenzaldehyde-monosorbitol acetals; alkali metal and alkaline earth metal salts of the acetates, propionates and lactates; and mixtures thereof. Also useful are polymeric materials such as, locust bean gum, sodium alginate, sodium caseinate, egg albumin, gelatin agar, carrageenin gum, sodium alginate, xanthan gum, quince seed extract, tragacanth gum, starch, chemically modified starches, semi-synthetic polymeric materials such as cellulose ethers (e.g. hydroxyethyl cellulose, methyl cellulose, hydroxypropyl cellulose, carboxymethyl cellulose, hydroxy propylmethyl cellulose), polyvinylpyrrolidone, polyvinylalcohol, guar gum, hydroxypropyl guar gum, cationic celluloses, cationic guars and the like and synthetic polymeric materials such as carboxyvinyl polymers, polyvinylpyrrolidone, polyvinyl alcohol polyacrylic acid polymers, polymethacrylic acid polymers, polyvinyl acetate polymers, polyvinyl chloride polymers, polyvinylidene chloride polymers and the like. Inorganic thickeners may also be used such as aluminium silicates, bentonites, or a mixture of polyethylene glycol and polyethylene glycol stearate or distearate. Naturally occurring polymers or biopolymers and their use are further described in European Application No. 522624, to Dunphy et al.

Hydrophobically modified celluloses are also suitable for use herein. These celluloses are described in detail in U.S. Pat. Nos. 4,228,277 and 5,104,646. Additional examples of suitable solidifying agents disclosed in the following references: U.S. Pat. No. 4,151,272, Geary, et al., issued Apr. 24, 1979; U.S. Pat. No. 4,229,432, Geria, issued Oct. 21, 1980; and U.S. Pat. No. 4,280,994, Turney, issued Jul. 28, 1981; U.S. Pat. No. 4,126,679, Davy, et al., issued Nov. 21, 1978; European Patent Specification No. 117,070, May, published Aug. 29, 1984; U.S. Pat. No. 2,900,306, Slater, issued Aug. 18, 1959; U.S. Pat. No. 3,255,082, Barton, issued Jun. 7, 1966; U.S. Pat. No. 4,137,306, Rubino, et al., issued Jan. 30, 1979; U.S. Pat. No. 4,154,816, Roehl, et al., issued May 15, 1979; U.S. Pat. No. 4,226,889, Yuhas, issued Oct. 7, 1980; U.S. Pat. No. 4,346,079, Roehl, issued Aug. 24, 1982; U.S. Pat. No. 4,383,988, Teng, et al., issued May 17, 1983; European Patent Specification No. 107,330, Luebbe, et al., published May 2, 1984; European Patent Specification No. 24,365 Sampson, et al., published Mar. 4, 1981; and U.S. patent application Ser. No. 630,790, DiPietro, filed Jul. 13, 1984.

Preservatives

Suitable traditional preservatives for compositions of this invention are alkyl esters of para-hydroxybenzoic acid. Other preservatives which have more recently come into use include hydantoin derivatives such as 1,3-bis(hydroxymethyl)-5,5-dimthylhydantoin, propionate salts, and a variety of quaternary ammonium compounds such as benzalkonium chloride, quaternium 15 (Dowicil 200), benzethonium chloride, and methylbenzethonium chloride. Particularly preferred preservatives are disodium EDTA, phenoxyethanol, methyl paraben, propyl paraben, sodium benzoate, imidazolidinyl urea (commercially available as Germall 1157), sodium dehydroacetate, capryl hydroxamic acid, caprylyl glycol, methyl propanediol, benzyl alcohol and mixtures of the prior disclosed (such as the Spectrastat series from Inolex). The preservatives should be selected having regard for the use of the composition and possible incompatibilities between the preservatives and other ingredients in the emulsion. Preservatives preferably are employed in amounts ranging from about 0% to about 5%, more preferably from about 0.01% to about 2.5%, and most preferably from about 0.01% to about 1%, by weight of the composition.

Fragrance

The present concealer composition may include a fragrance. While not wishing to be bound by theory, it is believed that extending the life of the fragrance by using a fragrance technology helps reinforce the long wear benefits of the concealer. Suitable fragrance technologies include cyclodextrins (beta, gamma, alpha and derivatives), plus those whereby the fragrance is entrapped within solid entrapping particles as described in U.S. Publication No. 2009/0098170 filed by D'Acchioli, et al on Oct. 15, 2008.

Concealer Remover

As discussed above, high concentrations of PHR and tall oils may reduce the solubility of the semi-permanent concealer in soap and water. Conventional concealer formulations keep the concentration of these two components low to help ensure that the concealer can be washed off in soap and water. Accordingly, it may be desirable to provide a solvent-based concealer remover composition separately and/or in combination with the concealer (e.g., as a kit). The concealer remover may include at least 40% (e.g., at least 50%, at least 55%, or even 100%) of a solvent such as, for example, mineral oil, petroleum jelly, isododecane, silicones, other hydrocarbon solvents and mixtures thereof. One suitable example of a concealer remover is COVERGIRL CLEAN brand makeup remover available from The Procter & Gamble Company.

Packaging

The semi-permanent concealer composition may be packaged alone or in combination with a concealer remover. In one embodiment, a concealer kit comprises a package, wherein a first portion of the package contains the present semi-permanent concealer composition and a second portion of the package contains a concealer-remover composition. The package may include indicia which communicates the long-wear benefit of the concealer composition to a consumer. For example, the indicia may include a certain number of hours the product may last, for example, 24 hours, 36 hours, or 48 hours. Or, the indicia may include an hourglass and/or a clock graphic. The indicia may be in a form selected from the group consisting of a label, a graphic, a three-dimensional shape, and combinations thereof. In certain embodiments, the package may be in the form of a double-ended package, wherein the first end contains the semi-permanent concealer and wherein the second end contains the concealer-remover.

Method of Use.

The present semi-permanent concealer provides long-lasting coverage of skin imperfections such as tattoos, blemishes, veins, or bruises on various parts of the body (e.g., face, arms, legs and back). Thus, when a user identifies a particular target skin area for coverage, the user will select an appropriate color and/or shade of concealer and apply it to the target skin area. Typically, the target skin area to which the concealer is applied will be relatively small. However, it is to be appreciated that the present concealer may be applied to larger areas of skin, as desired. The concealer may be applied to the skin with the fingers or with a suitable applicator (e.g., roller device, dauber, sponge or the like). Examples of applicator devices that may be suitable for use herein are disclosed in U.S. Provisional Ser. No. 61/523,588, filed by Wilson, et al., on Aug. 15, 2011. Once applied, the user may use spread the concealer across the target skin area to provide the desired level of coverage. In certain, embodiments, the film may be spread across the target area to form a flexible film that has an average film thickness of less than 40 microns. The applied concealer may provide a suitable level of cosmetic benefit for more than 24 hours.

When the target skin area is disposed on the body, as opposed to the face, the concealer may provide a suitable level of coverage for more than two days, three days, four days, or even five days. The present concealer may even provide multi-day coverage after one or more cleaning, showering or shaving events. For example, a user may apply the present concealer to a target skin area (e.g., on the leg) and then expose the target skin area to typical showering event two, three, four or even five days later. During a typical showering even the target skin area may be exposed to a significant amount of water along with a variety of common personal cleansing products (e.g., shampoo, conditioner, soap, body wash, facial cleanser, moisturizers and the like). During a typical showering even, the target skin area may also be exposed to a shaving event during which a razor or the like is used to remove unwanted hair in the target skin area. In addition to the razor itself, the target skin area may also be exposed to shaving cream or other lubricants or shaving aids commonly used before, during or after shaving. If a user does not wish to wait to for the present concealer to wear off over time, the concealer may be removed with a suitable solvent remover such as, for example, the concealer remover described hereinabove.

In certain embodiments, it may be desirable to use the present concealer as part of a multi-step personal care regimen. For example, the present concealer may be applied first a target skin area followed by the application of a second composition such as a foundation, which is applied to a broader target area that includes the smaller concealer-containing area. In this example, the foundation may be selected to further reduce any tacky feel that may be caused by the concealer.

TEST METHODS

In the Example section below, semi-permanent concealer compositions of the present invention are tested against conventional concealer compositions (products that are or were recently offered for sale to the public). The comparative testing shows the superior long-wearing characteristics of the present semi-permanent concealer compositions. The rub test provides a method for measuring the change in L-value on the L*C*h color scale to quantify the long-wear characteristics of a concealer. A lower Delta L value indicates that less of the concealer has rubbed off, relative to a concealer with a higher Delta L value. In other words, a lower Delta L value indicates superior long-wear characteristics.

Rub Test Method
Equipment:
Smooth substrate for supporting the film for testing (e.g., 10"×5½" Leneta Form 2A Opacity Chart) 0.006" draw down bar
Draw down board (ie., hard, flat surface suitable for supporting the Leneta chart and film sample).
White paper towel (or similar substrate) with sufficient strength to withstand test (e.g., WypAll L40 brand paper towels available from the Kimberly-Clark Corporation)
2½" diameter 2 kg weight
2½" diameter arch punch
Scissors
50° C. Oven
Double sided tape
Spectrophotometer (e.g., Datacolor Microflash 200d)

Procedure:
1. Drawdown Preparation:
   a. Place a Leneta chart on a drawdown board, black/white side up to provide a suitably smooth surface that will not undesirably impact film thickness. Label the top right of the card with sufficient sample & solvent identification. Take care to touch the card as little as possible since skin oils can affect the film thickness of product on the card.
   b. Apply 1-2 ml of product in a line across the top of the card, and use a 0.006" drawdown bar to draw a film down the entire length of the card.
   c. Repeat steps 1a & 1b for all products to be tested.
   d. Once all draw downs have been completed, place them in a 50° C. oven for two hours. Take care not to mar the film surfaces.
   e. After an hour, remove the samples from the oven and allow them to equilibrate to ambient room temperature.
2. Sample Abrasion:
   a. Use an arch punch to punch out 2½" diameter "abrasion disks" from the paper towel. Other substrates with similar abrasive characteristics may also be used, but it is important that the substrate is sufficiently white to contrast with the test sample. Suitable substrates should have an L-value of at least 82—on the L*C*h color scale.
   b. Completely and evenly, (do not overlap) apply strips of double sided tape to the bottom of the 2 kg weight. Cut away excess tape that extends beyond the perimeter of the weight bottom. Place and adhere a single abrasive disk (1 ply thickness) to the tape on the bottom of the weight. This will be used to abrade the film and see how much of it is removed.
   c. Place the disk/weight in the center of the first 3"×3" testing area. Twist the disk through two full revolutions in ⅛ revolution increments. Carefully remove the weight (up and away from the drawdown), and remove the abrading disk from the bottom of the weight. (Only change the double sided tape when a disk will no longer firmly adhere to the bottom of the weight.)
   d. Perform steps 2a, 2b, & 2c for all subsequent Leneta card drawdowns.
3. Color Measurement. The procedure below is described by using a Datacolor Microflash 200d brand spectrophotometer, but one of ordinary skill in the art will appreciate that other spectrophotometer capable of measuring a ΔL value on the L*C*h color scale may be equally suitable.
   a. Turn on the spectrophotometer.
   b. Press the 'Menu' key on the front of the spectrophotometer until the word "Set-up" appears.
   c. Click the button directly below the word "set-up" to select the set-up menu.
   d. Use the arrow keys to pick the calibration program.
   e. Set the 'hand-held head' to Specular Included. (Using the toggles on the head, confirm that "white" (vs black) is showing through port.)
   f. The calibration program prompts you to place the white tile under the spectrophotometer head and press the trigger.
   g. The prompt that instructs you to measure the Black Trap. Place the black trap under the head and squeeze the trigger.
   h. The calibration is now complete.
   i. Using the toggles on the back of the spectrophotometer's hand-held head, set the Specular to "Excluded". (Confirm that "black" is showing through the port.)

j. Select 'Illuminant' from the Main Menu. Use the D65/10 setting.
k. Select Display from the main menu. Select CIE LCH Data and choose add.
l. To take measurements, press the large Menu Key on the front of the spectrophotometer.
m. Select 'STD' from the menu. Select 'Temporary Standard'. Place the spectrophotometer over an unused abrasive disc over the white section of an unused Leneta card and take a reading by squeezing the trigger. This measurement is now set as the standard.
n. Place an abrasive disc that has abraded a product film over the white section of an unused Leneta card then place the spectrophotometer over the disk and take a reading by squeezing the trigger.
o. Record the Delta L value. Take 2 additional measurements of the sample, measuring a different area of the disk each time. The reported result for the test is the absolute value of the average of the 3 measurements.

EXAMPLES

Table 1 illustrates several representative semi-permanent concealer compositions designated as prototypes A-F.

TABLE 1

| Phase | Raw Material Name | Prototype A | B | C | D | E | F |
|---|---|---|---|---|---|---|---|
| A | Isododecane | 56.495 | 51.495 | 61.495 | 56.495 | 51.495 | 55.495 |
| A | Symdiol | 1.000 | 1.000 | 1.000 | 1.000 | 1.000 | 1.000 |
| A | Tall Oil Glyceride | 7.500 | 7.500 | 7.500 | 15.000 | 15.000 | 7.500 |
| A | Pentaerythrityl Hydrogenated Rosinate | 7.500 | 7.500 | 7.500 | | 15.000 | 7.500 |
| A | Shin-Etsu KSG-42 | | 8.000 | | | | |
| B | Disteardimonium Hectorite | 8.000 | 8.000 | 8.000 | 8.000 | 8.000 | 8.000 |
| C | Polyethylene AC-617A | 10.000 | 7.000 | 5.000 | 10.000 | | 10.000 |
| C | Micronized Black Iron Oxide | 0.180 | 0.180 | 0.180 | 0.180 | | 0.180 |
| C | Unipure Black | | | | | 0.180 | |
| C | Micronized Yellow Iron Oxide | 0.550 | 0.550 | 0.550 | 0.550 | 0.550 | 0.550 |
| C | Micronized Red Iron Oxide | 0.270 | 0.270 | 0.270 | 0.270 | 0.270 | 0.270 |
| C | Anatase Titanium Dioxide | 8.505 | 8.505 | 8.505 | 8.505 | 8.505 | 8.505 |
| C | Spheron LP-230 | | | | | | 1.000 |
| | Total: | 100.000 | 100.000 | 100.000 | 100.000 | 100.000 | 100.000 |

Phase A ingredients are melted and mixed together with low shear mixing. Phase B is gradually added to Phase A and then dispersed with high shear mixing. Phase C is then added and dispersed with high shear mixing. The batch is cooled to ambient conditions.

The long-wear characteristic of the present semi-permanent concealer composition is illustrated in Table 2. As illustrated in Table 2, Example F from Table 1 and two conventional concealer products were subjected to the Rub Test. The conventional mascaras are MAYBELLINE SUPERSTAY 24 HOUR brand concealer and COVERGIRL FRESH COMPLEXION brand concealer. The WYPALL brand paper towel used in the test had an L value of 96.2 on the L*C*h color scale.

TABLE 2

| Product | Delta L value |
|---|---|
| Representative Example F | 1.3 |
| MAYBELLINE SUPERSTAY 24 HOUR | 28.3 |
| COVERGIRL FRESH COMPLEXION | 29.8 |

As can be seen in Table 2, the present concealer composition clearly exhibits superior long-wear characteristics relative to the conventional concealer compositions.

Figure 3:
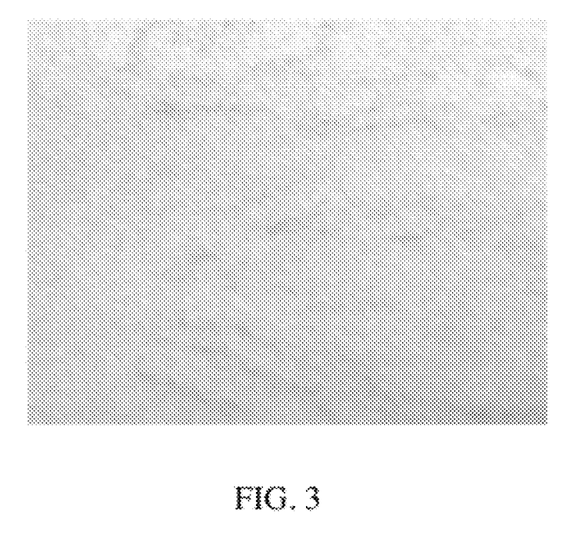
FIGS. 3-6 are images of a target skin area.
Figure 4:
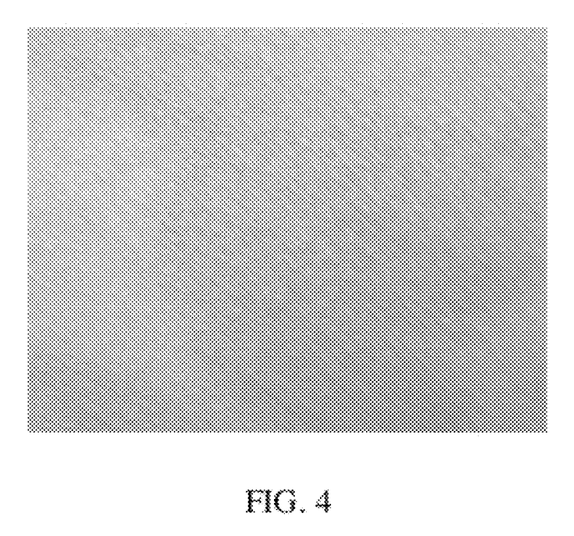
Figure 5:
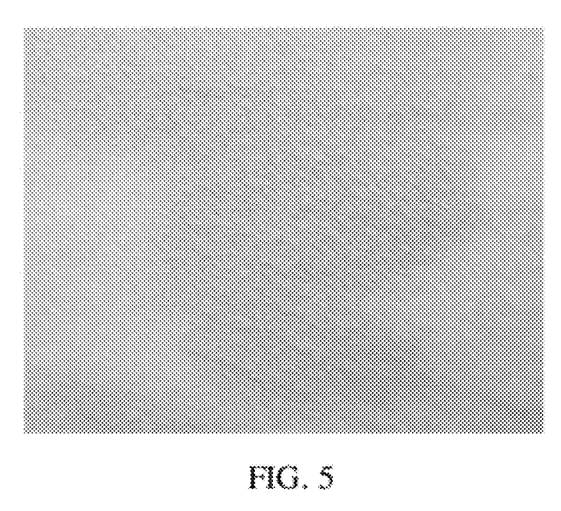
Figure 6:
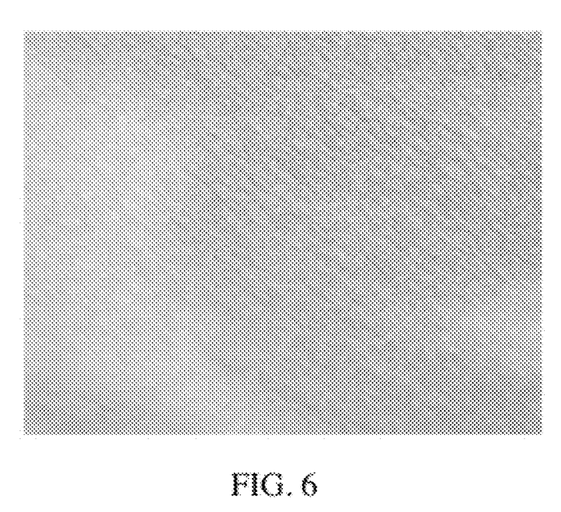

FIGS. 3-6 illustrate the long-wear characteristics of the present concealer composition when applied to the leg of test subject. The concealer used was prototype F. FIG. 3 shows an image of a target skin area on the leg of a test subject that was captured prior to applying the present concealer composition. As seen in FIG. 3, veins and other undesirable discoloration are visible in the target area. FIG. 4 shows an image of the target area immediately after application of the concealer. As can be seen in FIG. 4, the veins and undesirable discoloration are not visible. FIGS. 5 and 6 show images of the target area 1 day and 4 days after application of the concealer, respectively. As can be seen in FIGS. 5 and 6, the concealer is still intact and the veins and other undesirable discoloration are still concealed in the target area.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A semi-permanent, wax-free concealer consisting essentially of:
   a. from about 10% to about 80% by weight of a non-aqueous carrier which includes at least one of a silicone gum and polydimethylsiloxane;
   b. from about 15% to about 35% by weight of a film-forming tackifier comprising pentaerythrityl hydrogenated rosinate at between 0.1% and 99.9% by weight based on the weight of the tackifier and tall oil glyceride at between 99.9% to 0.1% by weight based on the weight of the tackifier; and
   c. from about 0.1% to about 20%, by weight, of iron oxide colorant particles having a particle size less than 30 microns;
   d. from 1% to 25% by weight of disteardimonium hectorite particles having a particle size less than 10 micron as a thickener;
   wherein the film-forming tackifier and the particles are dispersed in the carrier to form a single-phase anhydrous dispersion, wherein the weight ratio of tackifier to particles in the anhydrous dispersion is from about 2:3 to about 100:1; and the volume concentration of solid particles present in the composition is less than the critical pigment volume concentration; wherein said concealer has a Delta L value, of less than 20.0 according to the Rub Test.

2. The semi-permanent concealer of claim 1, further comprising a skin-conditioning agent.

3. The semi-permanent concealer of claim 2, wherein the skin conditioning agent is an alpha-hydroxycarboxylic acid, a beta-hydroxycarboxylic acid, salts of these acids, or combinations thereof.

4. A method for treating a target skin area, the method comprising:
   a. identifying a target area of skin in need of treatment; and
   b. applying the semi-permanent concealer of claim 1 to the target area.

* * * * *